United States Patent [19]

Koga et al.

[11] Patent Number: 5,240,864

[45] Date of Patent: Aug. 31, 1993

[54] METHOD OF ASSAYING OR ANALYZING SUBTYPES OF HUMAN LEUKOCYTE INTERFERONS OR THEIR ANTIBODIES, AND ANTIBODIES TO BE USED THEREFOR

[75] Inventors: Junichi Koga; Hiroyuki Shirono; Akio Matsuo, all of Kobe; Hajime Hiratani, Sennan, all of Japan

[73] Assignee: JCR Pharmaceuticals Co., Ltd., Hyogo, Japan

[21] Appl. No.: 621,825

[22] Filed: Dec. 4, 1990

[30] Foreign Application Priority Data

Jul. 12, 1989 [JP] Japan .................................. 1-320275

[51] Int. Cl.⁵ .......................................... G01N 33/531
[52] U.S. Cl. ..................................... 436/547; 436/543
[58] Field of Search ......................................... 436/547

[56] References Cited

PUBLICATIONS

Dalton et al–Chem. Abst. vol. 96 (1982) p. 102 131t.

*Primary Examiner*—Sam Rosen
*Attorney, Agent, or Firm*—Burgess, Ryan & Wayne

[57] ABSTRACT

Antiserum which can recognize all subtypes of human leukocyte interferon is prepared from the blood of an animal immunized with partially purified human leukocyte interferon obtained from a culture of human leukocyte stimulated with Sendai virus.

The antiserum is added to a column whereon concentrated culture broth of human leukocyte has been immobilized to adsorb impurities, the effluent is added to a column whereon partially purified human leukocyte interferon has been immobilized to adsorb anti-human leukocyte interferon antibody and then the antibody is eluted from the column.

The antibody thus obtained recognizes all subtypes of human leukocyte interferon and can be separated by a chromatography to each monoclonal antibody which recognizes a single subtype.

Employing these antibodies, the subtypes of human leukocyte interferon or their antibodies in a sample can be analized or assayed.

11 Claims, 4 Drawing Sheets

METHOD OF ASSAYING OR ANALYZING SUBTYPES OF HUMAN LEUKOCYTE INTERFERONS OR THEIR ANTIBODIES, AND ANTIBODIES TO BE USED THEREFOR

BACKGROUND OF THE INVENTION

1. Field of the Invention

The present invention relates to a method of assaying or analyzing subtypes of interferons derived from human leukocytes and antibodies against the said subtype, and to materials being usable for the method.

2. Description of the Related Art

Human leukocyte interferon, also called human interferon alpha, is known to exhibit antiviral and anti-tumor activities, and its clinical application has already been started. The recently commercialized genetic engineering has quickly been applied for the product and prompted greatly the analyses of the genes for interferons. The human interferons are classified into three types, or alpha, beta and gamma, according to the differences in kind of the cells from which they are derived and their physico-chemical properties. With reference to the beta-interferon, two molecular species have been reported to exist, while one molecular species has been described for the gamma-interferon. In contrast to these interferons, the alpha-type of interferon is known to exist as a great variety of subtype as many as more than 20 kinds (Goeddel et al., Nature, 287, 411 (1980). Pestka et al., 1987 Annual Review of Biochemistry, 56, 727), and extensive investigation has been carried out into the commercialization of the said interferon. As an analysis for such interferons, however, there has been used a extremely complicated technique which comprises purifying each of the subtypes to a high degree of purity, followed by amino acid sequencing (Rubinstein et al., Proc. Natl. Acad. Sci. USA, 76, 640 (1979)). The individual subtype, although containing a particular amino acid sequence in common, differ each from the other partially in amino acid sequence and have been clarified to be mutually independent gene expressions. In exerting the activities, they offer different specific features in species-specificity spectrum of antiviral activity, etc., and are considered to share physiological activities or cooperate among each other in some form in living body. Nevertheless it is quite difficult to except that such subtypes allow all of their genes to undergo expression in living body, and though the protein sequencing analysis of the subtypes presents an important problem in the analysis of their activities, the lack of a simple and convenient analytical technique has made the range of findings extremely restricted and limited in this field (Adolf et al., J. Gen. Virol., 68, 1669 (1987)). After recombinant alpha-type interferon produced by use of genetic engineering has been initiated to be applied to humans, in addition, the production of neutralizing antibody against interferons is in recent years observed at high frequencies.

In view of the fact that recombinant interferon is composed in nature of a single subtype, the incidence of such a kind of antibodies is assumed to nullify the effect of the administered interferons, and can be considered the critically serious problem from the viewpoint of clinical application. Also, such a kind of antibodies is thought to neutralize the activities of the interferons that the human body produces as a part of its own defense mechanism, and is presenting an entirely novel category of problem. Yet, the lack of an effective evaluation procedure of antibodies has resulted in failure to accumulate relevant findings. As is stated above, the development of a simple, convenient and quick analyzing method for the subtype compositions and antibodies is in strong demand from the standpoints of fundamental science and clinical application. For the purpose of analyzing all the naturally occurring subtypes, it is necessary to prepare the antibody using as an antigen the partially purified interferons containing all subtypes. In preparing the antibody, it is preferable to immunize two species of animals in order to establish an analysis technique based on the sandwich type enzyme-antibody assay through the two-antibody method, but it may also be possible to prepare the antibody with use of one species of animal, followed by direct enzyme-labelling of part of the antibody to perform sandwiching. In either case, the resulting antibody must be a polyclonal antibody capable of recognizing all the subtypes. For the purpose of this, it may be possible to use a suitable mixture of monoclonal antibodies against individual subtype, but it is difficult to establish the hybridomas which can produce such antibodies. This is because this technique suffers the defects that (1) all the subtypes of interferons must be isolated and purified in fairly large quantities, (2) individual cell fusions must be effected, (3) the cells capable of producing the antibodies must be screened and furthermore the resulting antibodies can only recognize one antibody-determining portion out of the protein of each subtype, leading to a very fair possibility of escaping detection in the case of subtype produced only in very minute quantities. In the case of a polyclonal antibody against leukocyte interferon, contamination with antibodies against impurities contained in the purified sample is likely to take place, and this must be absolutely avoided.

SUMMARY OF THE INVENTION

The present inventors found that all the subtypes contained in the unpurified culture broth (crude interferon solution) of human leukocytes were present in partially purified human leukocyte interferon, and on the basis of this finding, prepared an antibody using them. Further purification through absorption of such antibody led to the discovery that there can be obtained the highly specific antibody against leukocyte interferon which recognizes all the subtypes of interferon but not any antigen other than these at all. Thereafter, the present inventors established the technique of high performance liquid chromatography (HPLC) which can permit simple but efficient fractionation of subtypes of interferons from one subtype to another. And it was further clarified that the enzyme-antibody method through the combination of these findings can perform exceedingly simplified detection of the subtype compositions similar to the biological activities, and these have permitted completion of the present invention. This invention is concerned with a process of producing an antiserum capable of recognizing all the subtypes of human leukocyte interferons, characterized in that said process comprises immunizing an animal with partially purified human leukocyte interferon obtained from a culture product of human leukocytes stimulated with Sendai virus, followed by collection of serum from the animal; a process of producing a polyclonal antibody capable of recognizing all the subtypes of human leukocyte interferons, characterized in that said process comprises passing an antiserum, as obtained by the above-described process, through a column having a concentrated culture broth of human leukocytes immobilized thereon to thereby absorb an antibody against human leukocyte interferon and then washing the column, followed by elution of the above antibody; and a method of analyzing the said antibody, characterized in that said method comprises detecting an antibody against a subtype of leukocyte interferon in a sample through the antigen-antibody reaction using the said subtype as fraction-collected by means of column chromatography.

DESCRIPTION OF THE PREFERRED EMBODIMENTS

Human leukocytes are suspended in a suitable culture medium (for example, Ham F12 culture medium), and the resulting suspension is admixed for example with a suitable quantity (50 to 200 HA) of Sendai virus, followed by cultivation to thereby produce crude interferon. The above procedure can be performed by means of the known method (Cantell et al., Methods in Enzymology, 78, 29 (1981)). Subsequently, the crude interferon can further be purified with use of a technique (Cantell et al., ibid., 499) consisting of combination of precipitation with an alkali rhodanide such as potassium rhodanide under acidic conditions and ethanol precipitation to thereby give partially purified human leukocyte interferon.

The partially purified interferon obtained by the above-described procedure, when used to immunize an animal, can yield, in the form of its serum, an antiserum containing antibodies against all the subtypes of human leukocyte interferon. Though removal of antibodies against impurities contained in such polyclonal antibody has heretofore constituted an extremely difficult problem, it now has been proven that the problem can be solved by enhancing specificity through affinity chromatography using an impurity immobilized column and an interferon-immobilized column.

In the present invention, the antiserum as obtained by the above procedure is passed through a column having a concentrated culture broth of human leukocytes immobilized therein to remove antibodies against impurities, and the effluent is passed through a column having the above-stated, partially purified human leukocyte interferon immobilized therein to absorb the antibody against the human leukocyte interferon, whereupon the column is washed, followed by elution for the antibody. For the elution, for example, there can be used a buffer composed of 0.1M citric acid-0.5M sodium hydrochloride. The resulting antibody can be purified by use of protein A Sepharose, etc. as is conventionally the case with this field of art. In cases where the subtype of leukocyte interferon is analyzed by use of the sandwich immunoassay method, leukocyte interferon must in the first place be fractionated. For the purpose of this, a variety of chromatographic technique can be applied, and HPLC using a reverse-phase column can perform the best separation and is the most suitable in terms of reproducibility and quickness. In the case of conveniently simplified testing, for example, an antibody (antibody A, e.g. equine antibody) against leukocyte interferon is coated in advance on a microplate provided with 96 holes, and a highly concentrated protein solution, such as 1% bovine serum albumin solution, is distributed in suitable volume. The eluate from the column, as divided into fractions in accordance with the retention time, is collected in each hole of the thus prepared plate. After a suitable length of time is allowed, the plate is washed, and the reaction is allowed to proceed with a diluent of an antibody (antibody B, e.g. caprine antibody) derived from an animal of a species different from the one from which the antibody used for coating is obtained. After the plate is washed again, the reaction is allowed to proceed with an enzyme-labelled antibody against the antibody B. After the above described procedure is performed, the enzymatic activity becomes detectable in the holes where either subtype of interferon is present. Strength of enzymatic activity can be measured in terms of the extent of coloration. Alternatively, a substrate is added to the plate as such, whereupon strength of enzymatic activity can be quickly measured by means of a plate reader. Also, the extent of coloration can be plotted as a function of a length of time of elution from the column to prepare a graph, which can not only facilitate analysis of the subtype existence pattern but also enables their ratio to be quantitatively determined quickly and simply. Furthermore, a patient serum being used as the antibody B can be treated with anti-immunoglobulin of human origin or protein A which has been enzyme-labelled to thereby detect the antibody in the patient serum and also to analyze its specificity easily.

Thus, according to the present invention, there are provided the antisera and polyclonal antibodies capable of recognizing all the subtypes of human leukocyte interferon as well as the simplified method of assaying and analyzing the said subtypes and their antibodies in a specimen with use of the same.

Referring to the drawings, FIG. 1 shows the results of SDS gel electrophoresis with the partially purified human leukocyte interferon as obtained in Example 2, followed by allowing the proteins on the gel to migrate electrically to a nitrocellulose membrane to thereby perform the Western blotting, wherein A and B designate the results in the cases of equine serum against human leukocyte interferon and purified equine antibody against human leukocyte interferon, respectively, with the lanes 1 and 2 indicating electrophoretic transfer under reductive and non-reductive conditions, individually.

The present invention is explained further by the following examples.

EXAMPLE 1

Figure 1:
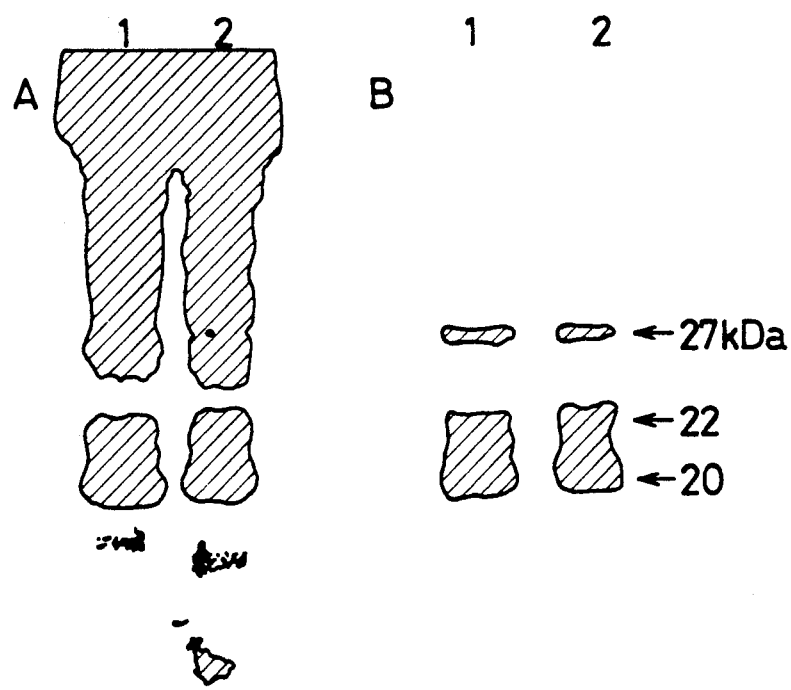

Fresh blood, drawn within 48 hours, was centrifuged at 2,600 rpm for 10 min, and the resulting leukocyte layer (buffy coats) was collected. Erythrocytes being mingled with leukocytes were allowed to undergo hemolysis by admixing the buffy coats with 9-fold volume of cold ammonium chloride solution (0.83%), followed by centrifugation to give purified leukocytes as a precipitate. The leukocytes were suspended in a culture medium at a concentration of $10^7$ cells/ml, whereby as the medium, there was used HAM F-12 Medium (produced by Flow Co.) being admixed with 4% of human serum freed from gamma-globulin and 50 ug/ml of gentamycin. Sendai virus was added to the suspension of human fresh leukocytes at the final concentration of 100 HA/ml, followed by incubation at 37° C. for 2 hours. Then, incubation was continued overnight at a temperature declined down to 28° C. The culture broth was centrifuged, and the resulting supernatant liquid was found to contain 50,000 units/ml to 200,000 units/ml of interferon ($10^4$ Int'l units/mg protein) and was to be used as a crude interferon solution. 100 liters of the crude interferon solution was admixed with potassium rhodanide (manufactured by Wako Pure Chemicals Ind. of Japan) to a final concentration of 0.5 mole, followed by adjustment to pH 3.5 to yield a precipitate. The precipitate was admixed with 20 liters of 95% cold ethanol, and the mixture was vigorously stirred in a blender to extract interferon contained in the precipitate. Proteins, particularly albumin, other than interferon was allowed to precipitate at a pH of 5.5 and removed through centrifugation, and then, the supernatant liquid was adjusted at pH 8.0 to give interferon in the form of a precipitate. The precipitate was dissolved in phosphate-buffered isotonic saline (pH 7.4) as formulated by Dulbecco to produce a partially purified interferon solution in yields of 30 to 80% ($10^5$ Int'l units/mg protein). The partially purified human leukocyte interferon obtained by this procedure was given to a goat and a horse for immunization. In performing the immunization, the interferon as brought into an emulsion with complete adjuvant was injected subcutaneously to the animals at the single dose of $2 \times 10^7$ units once a week for consecutively 3 months, with $2 \times 10^3$ units being applied as the final dosage, and one week later, blood samples were taken to give sera. The resulting antisera were found to show the antibody values as tabulated in Table 1.

solution, except that Sendai virus was no added, to thereby give a culture broth of human leukocytes. The culture broth was concentrated (5 mg/ml) and immobilized on 20 ml of bromium-cyanide activated Sepharose (manufactured by Pharmacia Co.), followed by packing into a column (1.5 cm in diameter×10 cm in length). The column (Mock column) was buffered with phosphate-buffered isotonic saline (PBS), and each of the antisera as obtained in Example 1 was passed through the column. This procedure removed antibodies against any antigens other than interferon through absorption on the column. By following the same procedure as described previously, a Sepharose column having the partially purified interferon immobilized thereon was prepared and after being buffered with PBS, was loaded with the effluent from the above Mock column. The column was washed well with PBS, and the absorbed antibody against interferon was eluted with an eluting solution composed of 0.1M citric acid-0.5M sodium chloride. This procedure permitted not only removal of antibody proteins against any antigens not being derived from the leukocyte culture broth but also concentration of the antibody against interferon. The resulting antibody was assayed for specificity by way of the Western blotting method (Towbin et al., Proc. Natl. Acad. Sci. USA, 76, 4350 (1976)), as is conventionally usual in this filed. The results are shown in FIG. 1. The interferon antibody after being purified showed specific blots only in the portions corresponding to the mobility of interferon. This procedure yielded the antibody that reacted only with human leukocyte interferon. Through the experiment to be described in Example 3, investigation was conducted to find out whether or not this antibody would be able to recognize every and all of the subtypes contained in a culture broth of human leukocytes being stimulated with Sendai virus.

TABLE 1

| | Equine serum | | | Caprine serum | | |
|---|---|---|---|---|---|---|
| | Volume ml | Neutral'n. value, /ml | Protein mg/ml | Volume ml | Neutral'n. value, /ml | Protein mg/ml |
| Serum | 100 | 50,000 | 60 | 130 | 60,000 | 55 |
| Impurity[1] | 280 | 15,000 | 3 | 350 | 18,000 | 5 |
| Interferon[2] | 15 | 250,000 | 18 | 15 | 310,000 | 28 |

Notes:
The neutralization value is expressed in terms of dilution ratio of antibody solution that permits 100 units/ml of interferon activity to be attenuated to 10 units/ml.
[1]in column effluent.
[2]in column eluate.

EXAMPLE 2

In order to produce an antiserum having extremely high specificity toward human leukocyte interferon, the following treatment was carried out: there was performed the same procedure as described in Example 1 for the preparation of crude interferon solution, except that Sendai virus was no added, to thereby give a culture broth of human leukocytes. The culture broth was concentrated (5 mg/ml) and immobilized on 20 ml of bromium-cyanide activated Sepharose (manufactured by Pharmacia Co.), followed by packing into a column (1.5 cm in diameter×10 cm in length). The column (Mock column) was buffered with phosphate-buffered isotonic saline (PBS), and each of the antisera as obtained in Example 1 was passed through the column. This procedure removed antibodies against any antigens other than interferon through absorption on the column. By following the same procedure as described in Example 1 for the preparation of crude interferon

EXAMPLE 3

Figure 2:
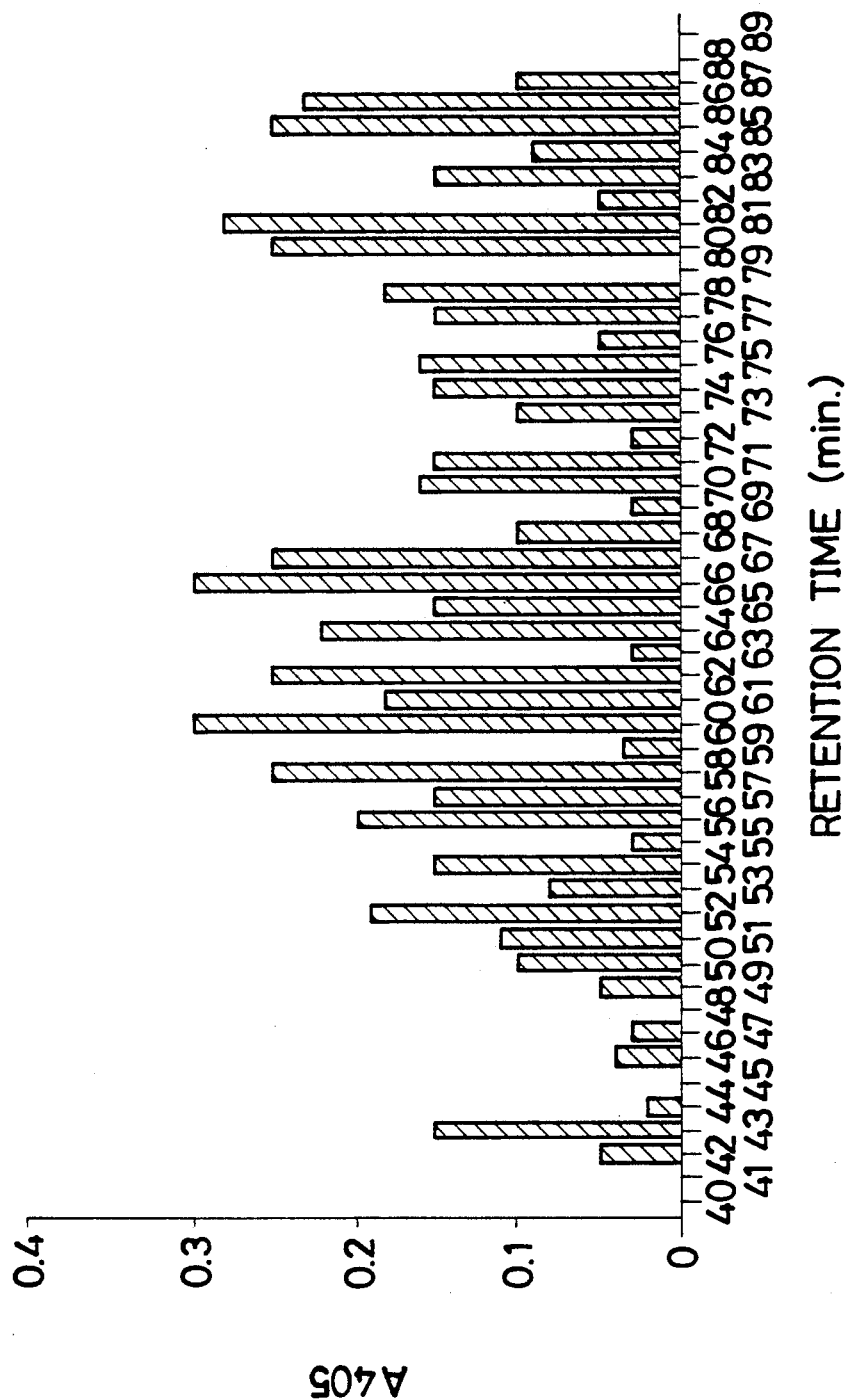
FIG. 2 and FIG. 3 are graphs showing the test results in Example 3, wherein FIG. 2 indicates peaks of HPLC fractions of human leukocyte interferon as measured with use of the antibody according to this invention, with FIG. 3 giving interferon activity peaks of the same HPLC fractions.
Figure 3:
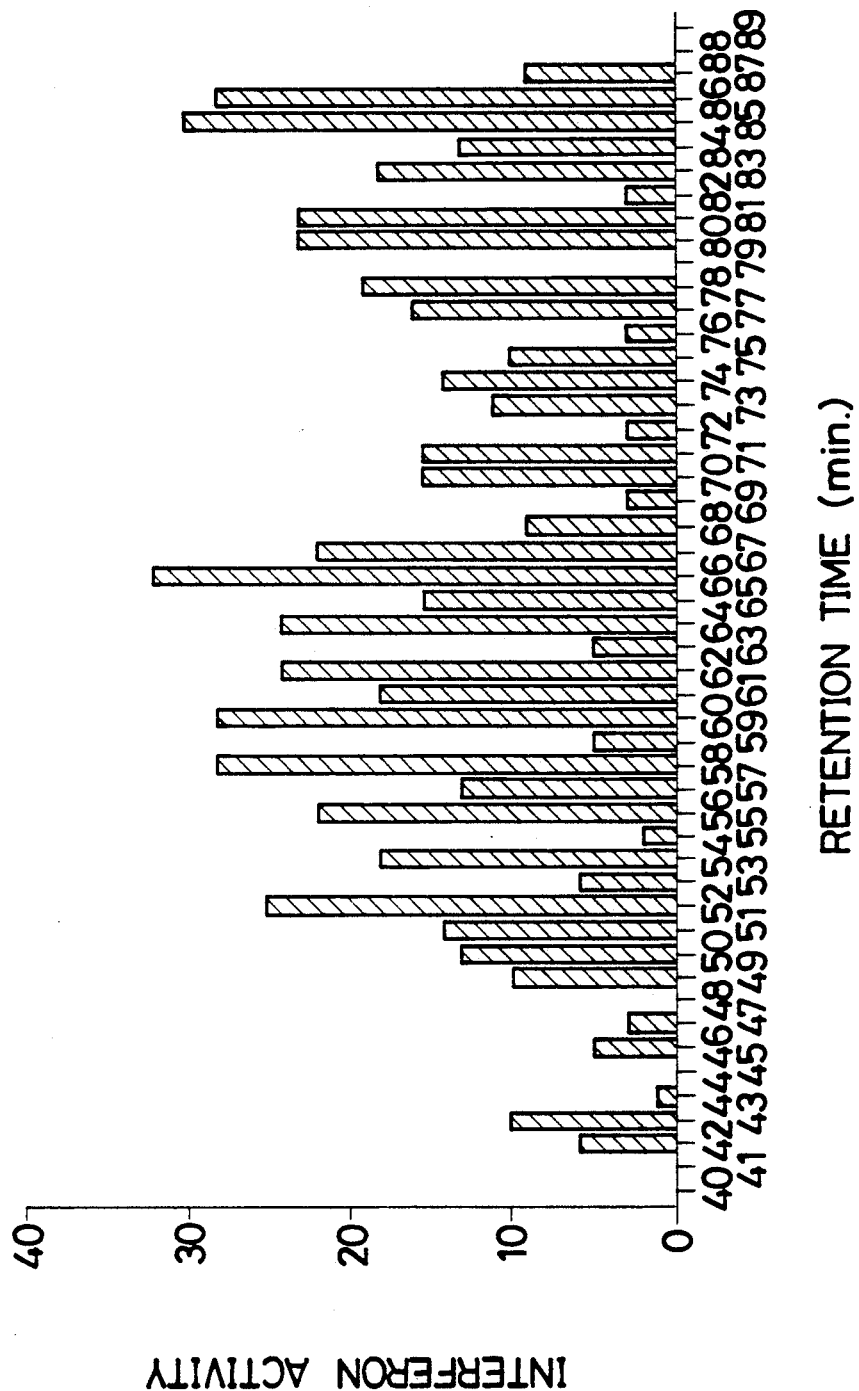

Using the antibody as obtained in Example 2, the enzyme-antibody method was performed; equine antibody against interferon was diluted to 0.1 ug/ml with PBS. The diluted antibody was distributed in 0.1 ml portion into each hole of a plate (manufactured by Nunc Co.) provided with 96 holes and maintained at 37° C. for 1 hour. The plate was inverted to discard the contents, and PBS (APBS) containing 1% of bovine serum albumin (manufactured by Sigma Co.) was distributed in 250 ul portion into each hole of the plate and maintained at 37° C. for 30 min. The HPLC eluate to be described below was collected into the individual holes of the plate in the order of a length of the column retention time. In conducting HPLC, the C18 column (Hipore RP-318, manufactured by Biorad) was loaded with 30 million units of human leukocyte interferon in the presence of 0.1% trifluoroacetic acid (manufactured by Wako Pure Chemicals Co.), and eluted with 25% to 75 5 gradient acetonitrile, followed by washing each hole three times with 250 ul of PBS (TPBS) containing 0.05% of a surfactant (Tween 20, manufactured by Biorad Co.). Caprine antibody against interferon was diluted with APBS to a concentration of 0.1 ug/ml, and the diluted antibody was distributed in 0.1 ml portion into the individual holes and maintained at 37° C. for 1 hour. After washing three times with TPBS, a 1,000-fold diluted solution of peroxidase-labelled anti-goatimmunoglobulin G (manufactured by kappel Co.) with APBS was distributed in the holes and maintained at 37° C. for 1 hour. After washing with TPBS, the holes were subjected to coloration by use of the peroxidase-substrate kit supplied by Biorad Co. The coloration patterns are shown i FIG. 2. For the purpose of reference, shown in FIG. 3 are the patterns of interferon activity (antiviral activity) for the eluates collected in the same manner. The antiviral activity was determined with the Diapty method using FL cells and VSV. The results revealed that all the peaks showing antiviral activity were detectable by means of the enzyme-antibody method utilizing the antibody as obtained by the procedure as described herein.

EXAMPLE 4

Figure 4:
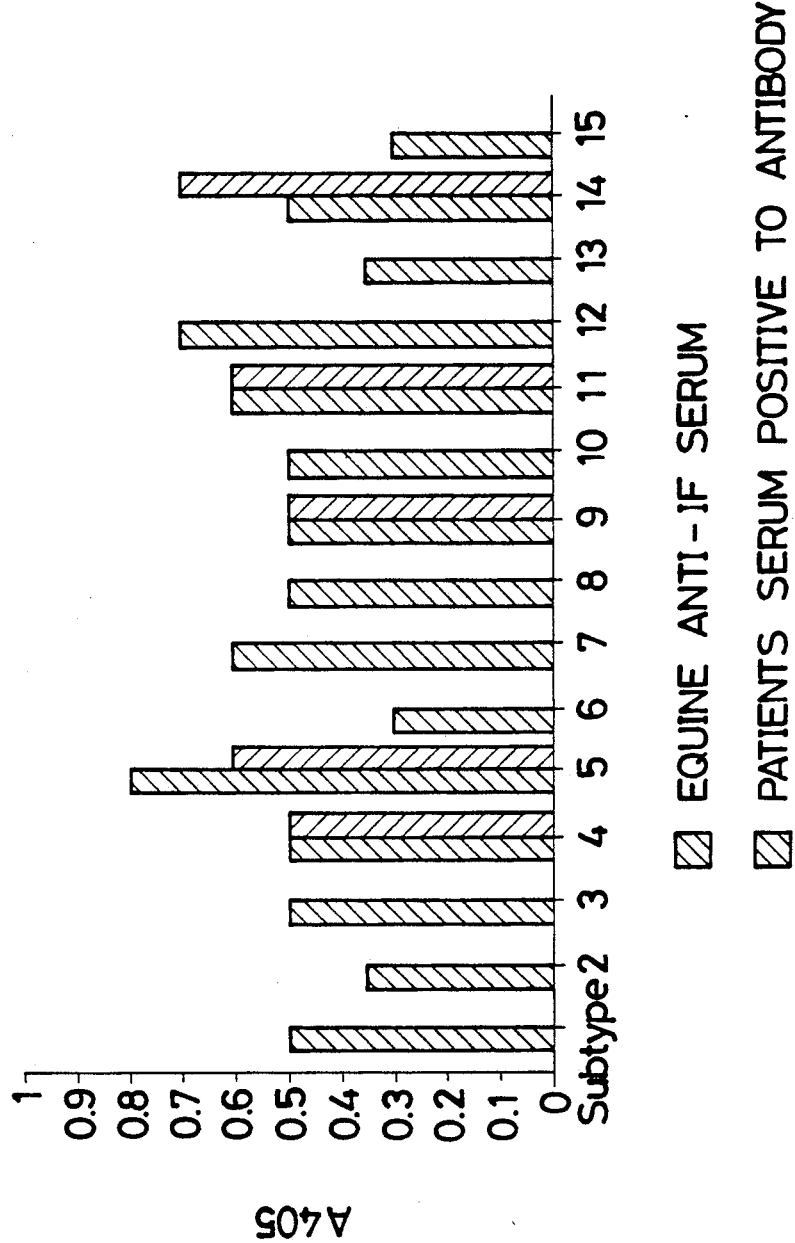
FIG. 4 is a graph showing the test results with a patient's serum being positive to the interferon antibody by use of the enzyme-antibody method while utilizing each of subtypes of interferons fraction-collected in advance.

A subtype derived from human leukocyte interferon as collected in advance was diluted with PBS to a concentration of 5 ug/ml, and the diluted subtype solution was distributed in 100 ul portion into each hole of a plate provided with 96 holes and maintained at 37° C. for 1 hour to allow immobilization. Then, APBS was distributed in 150 ul portion into the individual holes and maintained at 37° C. for 30 min to block non-specific adsorption. After the holes were washed with TPBS, a patient's serum which had been confirmed to contain the antibody against interferon was diluted 100-fold into APBS and the diluted solution was distributed in 100 ul portion into the holes. As a control, equine antibody against interferon was diluted with APBS to a concentration of 0.1 ug/ml and distributed in 100 ul portion into the holes. After being maintained at 37° C. for 1 hour, the holes were washed with TPBS, and a 1,000-fold diluted solution of alkaline phosphatase-labelled anti-human immunoglobulin G in APBS was poured in 100 ul portion into the individual holes, whereas a 1,000-fold diluted solution of alkaline phosphatase-labelled anti-horse immunoglobulin G (manufactured by Biosis Co. of France) in APBS was filled in 100 ul portion into the control holes. After maintaining at 37° C. for 1 hour and washing with TPBS, the holes were subjected to coloration with use of alkaline phosphatase substrate kits manufactured by Biorad Co. The results are shown in FIG. 4.

We claim:
1. A process of producing an antiserum capable of recognizing subtypes of human leukocyte interferons, which comprises steps of:
   (1) cultivating human leukocyte with Sendai virus,
   (2) centrifuging a culture broth obtained from step (1) to recover crude interferon solution;
   (3) adding an alkaline rhodanide to the solution under acidic conditions to yield a precipitate,
   (4) extracting the precipitate with ethanol,
   (5) adjusting the pH of the extract to about 8.0 to recover partially purified interferons as precipitates and
   (6) immunizing an animal with the partially purified interferons, and
   (7) thereafter obtaining antiserum from the animal's blood.

2. A process according to claim 1, wherein the antiserum is a product obtained by immunizing an animal with partially purified human leukocyte interferon which is obtained by purifying a culture of human leukocytes stimulated with Sendai virus by precipitation with an alkali rhodanide under acidic condition and ethanol precipitation, and recovering the serum from the animal.

3. A process of producing an antibody capable of recognizing subtypes of human leukocyte interferons, which comprises steps of:
   (1) cultivating human leukocyte with Sendai virus,
   (2) centrifuging a culture broth obtained from step (1) to recover crude interferon solution,
   (3) adding an alkaline rhodanide to the solution under acidic conditions to yield a precipitate,
   (4) extracting the precipitate with ethanol,
   (5) adjusting the pH of the extract to about 8.0 to recover partially purified interferons as precipitates,
   (6) immunizing an animal with the partially purified interferons and thereafter obtaining antiserum from the animal's blood,
   (7) removing antibodies against antigens other than interferons from the antiserum by passing the antiserum through a column for affinity chromatography wherein culture broth of human leukocyte obtained by cultivating human leukocyte without Sendai virus is immobilized to obtain purified antiserum and
   (8) removing antibodies against antigens, not originating from the culture broth of human leukocyte, from the purified antiserum by passing the purified antiserum through a column wherein the partially purified interferon obtained in step (5) is immobilized, and thereby obtaining a purified antibody capable of recognizing subtypes of human leukocyte interferons.

4. A method of assaying a subtype of human leukocyte interferon in a sample, which comprises allowing the polyclonal antibody obtained the process of claim 3 to act on the sample.

5. A method according to claim 4, wherein the said method is performed by use of the enzyme-antibody method.

6. A method according to claim 4, wherein the leukocyte interferon is a lymphoblast type interferon.

7. A method claim 4, wherein the leukocyte interferon is a recombinant interferon.

8. A method according to claim 5, wherein the enzyme-antibody method is the sandwich method.

9. A method according to claim 5 or 8, wherein said method is conducted by means of the sandwich method using the polyclonal antibody as obtained in claim 6 and which is obtained through immunization of two species of animals.

10. A method according to claim 4, wherein the specimen is one fractionated by column chromatography.

11. A method according to claim 10, wherein column chromatography is reverse-phase high performance liquid chromatography.